United States Patent [19]
Qiu

[11] Patent Number: 6,054,615
[45] Date of Patent: Apr. 25, 2000

[54] FLUORINATED QUATERNARY AMMONIUM SALTS

[75] Inventor: Weiming Qiu, Wilmington, Del.

[73] Assignee: E.I. du Pont de Nemours and Company, Wilmington, Del.

[21] Appl. No.: 09/321,317

[22] Filed: May 27, 1999

[51] Int. Cl.[7] ...................... C07C 211/63; C07C 211/08; C07C 233/13

[52] U.S. Cl. ........................... 564/291; 554/67; 564/209; 564/510

[58] Field of Search .................................. 564/291, 209, 564/510; 554/67

[56] References Cited

U.S. PATENT DOCUMENTS

| | | | |
|---|---|---|---|
| 2,727,923 | 12/1955 | Husted | 564/291 |
| 4,000,175 | 12/1976 | Foulletier et al. | 260/459 R |
| 4,059,629 | 11/1977 | Foulletier et al. | 260/583 GG |

FOREIGN PATENT DOCUMENTS

| | | | |
|---|---|---|---|
| 04164027 | 6/1992 | Japan | A61K 31/14 |

OTHER PUBLICATIONS

Takahashi et al., Chem. Abst. 127:177653, 1997.

Oshino et al., Chem. Abst. 117:198508, 1992.

Preussmann, P. et al., Fluoro–substituted N–nitosamines. 5. Carcinogenicity of N–nitroso–bis–(4,4,4–trifluoro–n–butyl) amine in rats, *Carcinogenesis*, 3, No. 10, 1219–1222, 1982.

German, L.S. et al., Decomposition of Ammonium Bases Containing Polyfluoroalkyl Groups, *Institute of Heteroorganic Compounds, Academy of Sciences of the USSR*, 173, No. 6, 1328–1331, Apr., 1967.

Yamanaka, H. et al., Reaction of (Polyfluoroalkyl)trimethylammonium Salts With Hydroxide Ion, *Journal of Fluorine Chemistry*, 52, 185–194, 1991.

*Primary Examiner*—Peter O'Sullivan

[57] ABSTRACT

Selected quaternary ammonium salts containing fluoroalkyl, preferably perfluoroalkyl, groups that are stable to bases are described. They are useful as phase transfer reaction catalysts, especially in basic media.

9 Claims, No Drawings

FLUORINATED QUATERNARY AMMONIUM SALTS

FIELD OF THE INVENTION

Selected novel fluorinated quaternary ammonium salts, and intermediates thereto, that are relatively stable to bases are described.

TECHNICAL BACKGROUND

Quaternary ammonium compounds, including fluorinated quaternary ammonium compounds (FQAC), are useful as "catalysts" in phase transfer reactions, that is reactions in which the bulk of one reactant resides in one liquid phase but the reaction takes place in another liquid phase, or at the interface between the phases. FQACs are particularly useful when one (or both) of the phases is itself fluorinated and/or one of the reactants is fluorinated. However some FQACs often have drawbacks that unfluorinated quaternary ammonium compounds usually do not have. For example some FQACs are unstable to bases which limit their use, see for instance H. Yamanaka, et al., Journal of Fluorine Chemistry, vol. 52, p. 185–194 (1985) and L. S. German, et al., Dokl. Akad. Nauk. SSSR, vol. 173, p. 1328–1331 (1967). Therefore improved FQACs are desired.

Various fluorinated amines and fluorinated quaternary ammonium salts are disclosed in R. Preussmann, et al., Carcinogenesis, vol. 3, p. 1219–1222 (1982); U.S. Pat. Nos. 4,059,629 and 4,000,175; and Japanese Patent Application 4-164027. These references do not disclose the compounds claimed herein.

SUMMARY OF THE INVENTION

Disclosed herein is a compound of the formula

A compound of the formula (I), (II), or (III) wherein formula (I) is

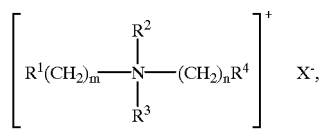

(I)

wherein formula (II) is

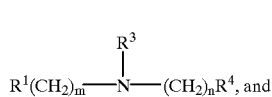

(II)

wherein formula (III) is

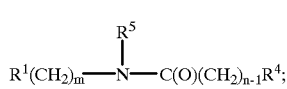

(III)

wherein:

m and n are each independently integers of 3 through 10;

$R^1$ and $R^4$ are each independently fluoroalkyl;

$R^2$ is alkyl;

$R^3$ is alkyl or $R^1(CH_2)_m$—;

$R^5$ is $R^1(CH_2)_m$—; and

X is an anion.

DETAILS OF THE INVENTION

By fluoroalkyl herein is meant an alkyl group substituted with at least one fluorine atom. Unless other wise stated, it is preferred that all alkyl and fluoroalkyl groups contain 1 to 30 carbon atoms.

In all the compounds herein it is preferred that:

$R^2$ is n-alkyl containing 1 through 10 carbon atoms, more preferably $R^2$ is methyl; and/or $R^1$ or $R^4$ is perfluoroalkyl, more preferably perfluoro-n-alkyl containing 1 though 10 carbon atoms, and most preferably both $R^1$ and $R^4$ are perfluoro-n-alkyl containing 1 though 10 carbon atoms; and/or X is halide; and/or m and/or n is 3; and/or m and n are the same.

The Examples illustrate various methods of making the claimed compounds. In general one can hydrogenate a fluorinated nitrile of the formula $R^4(CH_2)_{n-1}CN$ to the corresponding primary amine (see World patent Application 91/09025 and Japanese Patent Application 04-198157), convert the primary amine to a secondary amine using a Ru catalyst [B. T. Khai, et al., J. Organomelal. Chem., vol. 208, p. 249–251 (1981)], then alkylate to the tertiary amine (II) [R. N. Icke, et al., Org. Syn., vol. 25, p. 25 (1945), A. Kaluszyer, et al., J. Org. Chem., vol. 26, p. 3536 (1961)], and finally alkylate to the tertiary amine (I) using an alkyl halide. In another synthesis sequence a fluorinated nitrile of the formula $R^4(CH_2)_{n-1}CN$ is converted via standard chemistry to the corresponding acyl halide and then reacted with a secondary amine of the formula $[R^1(CH_2)_m]_2NH$ (which can be made by the first reaction sequence) to form the amide (III) wherein $R^3$ is $R^1(CH_2)_m$—. Alternatively (III) can be formed by converting the nitrile to an ester, and then reacting the ester with the amine. In either event (III) is then reduced with a compound such as $LiAlH_4$, $NaBH_4/H_2SO_4$ or $H_2$/bimetallic catalysts, wherein the $H_2$/bimetallic catalysts are a combination of a group 8 to 10 and group 6 to 7 transition metals. [C. J. Kibler, et al., Org. Syn. III, p. 108, C. V. Wilson, Org. Syn. IV, p. 564, and C. Hirosawa, Tetrahedron Lett., vol. 37, p. 6749 (1996)] to give (II). (II) can then be alkylated (as with an alkyl halide) to give (I).

(I) is useful as a phase transfer reaction catalyst. (II) and (III) are useful as chemical intermediates to make (I).

In the Examples, all pressures are gauge pressures. The following abbreviations are used:

b.p.—boiling point m.p.—melting point

RT—room temperature

THF—tetrahydrofuran

EXAMPLE 1

Hydrogenation of 3-Perfluorobutylpropionitrile with Raney-Co

A 210-ml shaker tube was charged with 30 g of $C_4F_9CH_2CH_2CN$ in 30 ml THF and 3.0 g of Raney cobalt in 5 ml THF. The vessel was closed, cooled, evacuated and pressured with hydrogen to 5.5 MPa. The vessel was heated to 110° C. and hydrogen pressure was adjusted to 10.3 MPa. The mixture was shaken for 16 h. The vessel was cooled and the gas was vented slowly. The contents were filtered and the filtrate was distilled to remove THF. The residue was distilled to give A (22.1 g, b.p. 115–142° C. mainly 137–142° C.), B (3.0 g, b.p. <100° C./270 Pa absolute), and C residue in pot 5 g. A is $C_4F_9CH_2CH_2CH_2NH_2$ with 1% THF and 1% of C. B is a 2:1 mixture of $C_4F_9CH_2CH_2CH_2NH_2$ and $(C_4F_9CH_2CH_2CH_2)NH$. C is $(C_4F_9CH_2CH_2CH_2)_2NH$. $(C_4F_9CH_2CH_2CH_2)_2NH$: $^{19}F$ NMR ($CDCl_3$) −81.6 (t, J=10 Hz, 6F), −115.1 (m, 4F), −125.0 (m, 4F), −126.6 (m, 4F) ppm. $^1H$ NMR ($CDCl_3$) 2.70 (t, J =6 Hz, 4H), 2.17 (m, 4H), 1.77 (m, 4H), 1.50 (br s, 1H) ppm. $^{13}C$ NMR ($CDCl_3$) 20.0, 28.8 (t, J=22 Hz), 48.5, 106.7–122.9 (m) ppm. MS (m/e) 537 ($M^+$, 0.4%), 536 ($M^+$−1, 1.8%), 518 ($M^+$−F, 8.2%), 290 (100%), 195 (1.6%), 169 (0.8%), 119 (2.9%), 69 (10.7%). Anal. Calcd. for $C_{14}H_{13}F_{18}N$: C, 31.29; H, 2.74; F, 63.65. Found: C, 31.51; H, 2.74; F, 62.75.

EXAMPLE 2

Hydrogenation of 3-Perfluorobutylpropionitrile with Ruthenium Boride

A 210 ml shaker tube was charged with 30 g of $C_4F_9CH_2CH_2CN$ in 30 ml THF and 4.0 g of RuB on activated carbon (2%). The vessel was closed., cooled, evacuated and pressured with hydrogen to 5.5 MPa. The vessel was healed to 110° C. and hydrogen pressure was adjusted to 10.3 MPa. The mixture was shaken for 16 h. The vessel was cooled and the gas was vented slowly. The cortents were filtered and the filtrate was distilled to remove THF. The residue was distilled at reduced pressure to give 4,4,5,5,6,6,7,7,7-nonafluoroheptylaniine (17.3 g, 57%, b.p. 94–97° C./24 kPa absolute), and di(4,4,5,5,6,6,7,7,7-noflafluoroheptyl)amine (6.3 g, 21%, b.p. 105–108° C./27 Pa absolute).

EXAMPLE 3

Hydrogenation of 3-Perfluorobutylpropionitrile with Platinum Boride

A 210-ml shaker tube was charged with 30 g of $C_4F_9CH_2CH_2CN$, 4.0 g of PtB on activated carbon (2%) and 30 ml THF. The vessel was closed, cooled, evacuated and pressured with hydrogen to 3.5 MPa. The vessel was heated to 110° C. and hydrogen pressure was adjusted to 10.3 MPa. The mixture was shaken for 16 h. The vessel was cooled and the gas was vented slowly. The contents were filtered and the filtrate was distilled to remove THF. The residue was distilled at reduced pressure to give 4,4,5,5,6,6,7,7,7-nonafluoroheptylamine (4.0 g, 13%, b.p. 94–97° C./24 kPa absolute) and di(4,4,5,5,6,6,7,7,7-nonailuoroheptyl)amine (20.5 g, 69%, b.p. 105–108° C./270 Pa absolute). The distillation residue (0.2 g) was mainly $(C_4F_9CH_2CH_2CH_2)_3N$.

EXAMPLE 4

Disproportionation of 4,4,5,5,6,6,7,7,7-nonafluoroheptylamine-Synthesis of Bis(4,4,5,5,6,6,7,7,7-nonafluoroheptyl)amine A 210-ml shaker tube was charged with 50 g of 4,4,5,5,6,6,7,7,7-nonafluoroheptylamine, $RuCl_3$ (0.75 g), $Ph_3P$ (1.9 g) and 50 ml THF. The mixture was heated at 245° C. for 24 h, then at 110° C. under 10.3 MPa hydrogen for 2 h. After being cooled to RT, the mixture was filtered to remove the catalyst. The filtrate was distilled to remove THF and distilled at reduced pressure to give bis(4,4,5,5,6,6,7,7,7-nonafluoroheptyl)amine, 36 g, 75%, bp 90–93° C./130 Pa (absolute).

EXAMPLE 5

Synthesis of Bis(4,4,5,5,6,6,7,7,7-nonafluoroheptyl)methylamine:

A solution of bis(4,4,5,5,6,6,7,7,7-nonafluoroheptyl)amine (3.0 g) and formic acid (90%, 1.5 g) was cooled in an ice-water bath and 8 ml of formaldehyde (37% weight) was added. The solution was slowly heated to 90° C. and maintained overnight. (Foaming and gas evolution at 60–75° C.) Concentrated hydrochloric acid (1 ml) was added and 7 ml of solution were removed by distillation. The remaining solution was cooled and treated with KOH (aq. 10%) to pH 11. The mixture was extracted with methylene chloride (3×50 ml). The combined methylene chloride extracts were washed with water (2×50 ml), dried over sodium sulfate, and concentrated on vacuum to give a residue. Distillation of the residue at reduced pressure gave 2.7 g of bis(4,4,5,5,6,6,7,7,7-nonafluoroheptyl)methylamine, yield 88%. $^{19}F$ NMR ($CDCl_3$) −81.7 (m, 6F), −115.1 (m, 4F), −125.1 (m, 4F), −126.6 (m, 4F) ppm. $^1H$ NMR ($CDCl_3$) 2.40 (t, J=6 Hz, 4H), 2.19 (s, 3H), 2.16 (m, 4H), 1.76 (m, 4H) ppm. $^{13}C$ NMR ($CDCl_3$) 18.4, 28.7 (t, J=23 Hz), 41.3, 56.5, 108–123 (m) ppm. MS (m/e) 532 ($M^+$−F, 7.5%), 382 (1.0%), 304 (100%), 195 (0.6%), 169 (0.8%), 119 (2.5%), 69 (9.4%).

EXAMPLE 6

Synthesis of Bis(4,4,5,5,6,6,7,7,7-nonafluoroheptyl)-dimethylammonium chloride

To a solution of bis(4,4,5,5,6,6,7,7,7-nonafluoroheptyl)methylamine (2.6 g) and 7 ml of ethanol was added methyl iodide (1.0 g, 7 mmol) at RT. The mixture was stirred at room temperature for 2 h and at 55° C. for 2 h. The solution was concentrated on a rotary evaporator to give solid ammonium iodide. [$^1H$ NMR ($CD_3OD$) 2.12 (m, 4H), 2.32 (m, 4H), 3.18 (s, 6H), 3.51 (m, 4H) ppm]. The iodide in methanol was converted to the chloride form by passing through a column packed with Amberlite® IRA 400 (Cl) ion exchange resin. The column effluent was collected and concentrated and dried under vacuum overnight to afford 2.5 g of product yield 83%, m.p. 70–72° C. $^{19}F$ NMR ($CD_3OD$) −80.9 (t, J=10 Hz, 9F), −113.7(m, 6F), −123.8(m, 6F), −125.5 (m, 6F)ppm. $^1H$ NMR ($CD_3OD$) 2.12 (m, 4H), 2.33 (m, 4H), 3.16 (s, 6H), 3.48 (m, 4H) ppm. $^{13}C$ NMR ($CD_3OD$) 15.7, 28.8 (t, J=23 Hz), 51.6, 64.6, 108–123 (m) ppm. Anal. Calcd. for $C_{16}H_{18}F_{18}NCl$: C, 31.94; H, 3.02; N, 2.33; Cl, 5.89. Found: C, 31.93; H, 2.95; N, 2.23; Cl, 5.70.

EXAMPLE 7

Synthesis of N-(4,4,5,5,6,6,7,7,7-nonafluoroheptyl -4,4,5,5,6,6,7,7,7-nonafluoroheptanamide A mixture of methyl 4,4,5,5,6,6,7,7,7-nonafluoroheptanoate (18 g 59 mmol) and 4,4,5,5,6,6,7,7,7-nonafluoroheptylamine (18.5 g, 66.8 mmol) was heated to slowly distill MeOH out through a 15 cm long column. Colorless liquid (10.5 g) was obtained by atmospheric and then full vacuum distillation. After being cooled to RT, the residue in the reaction flask was solidified to a yellow solid (26.0 g). NMR and GC-MS analysis indicated that it was the product, N-(4,4,5,5,6,6,7,7,7-nonafluoroheptyl)-4,4,5,5,6,6,7,7,7-nonafluoroheptanamide, 80% yield. $^{19}F$ NMR ($CDCl_3$) −81.6 (t, J=10Hz, 6F), −115.0 (m, 2F), −115.4 (m, 2F), −125.0 (m, 4F), −126.6 (m, 4F) ppm. $^1H$ NMR ($CDCl_3$) 1.85 (m, 2H), 2.12 (m, 2H), 2.42–2.61 (m, 4H), 3.38 (q, J=7 Hz, 2H), 5.70 (br s, 1H) ppm. $^{13}C$ NMR ($CDCl_3$) 21.0 (s), 26.9 (t, J=23 Hz), 27.3 (s), 28.5 (t, J=23 Hz), 39.0 (s), 170.0 (s), 115–122 (m) ppm. MS (m/e) 532 ($M^+$−F, 37.5%), 482 ($M^+$−$CF_3$, 0.3%), 382 ($M^+$−$C_3F_7$, 20.5%), 332 ($M^+$−$C_3F_7$, 58.7%), 275 (88.1%), 169 (1.8%), 119 (26.7%), 69 (100%).

EXAMPLE 8

Reduction of N-(4,4,5,5,6,6,7,7,7-nonafluoroheptyl)-4,4,5,5,6,6,7,7,7-nonafluoroheptanamide with $NaBH_4$ and $H_2SO_4$ A 250-ml 3-necked flask equipped with a stir bar, condenser, and addition funnel was charged with 26 g of N-(4,4,5,5,6,6,7,7,7-nonafluoroheptyl)-4,4,5,5,6,6,7,7,7-nonafluoroheptanamide, NaBH$_4$ (4.0 g), and THF (50 ml). To the mixture was added 4 ml of concentrated sulfuric acid in 20 ml Et$_2$O at ~0° C. The resulting mixture was refluxed for 3 hours. GC-MS analysis of the reaction mixture showed the formation of di(4,4,5,5,6,6,7,7,7-nonafluoroheptyl) amine along with less than 1% of the amide. KOH (10%, 30 ml) was added and the resulting mixture was stirred at rt. for 2 h. The mixture was extracted with methylene chloride (3×60 ml). The combined extracts were washed with water, dried over Na$_2$SO$_4$, and concentrated to give 24 g of a solid which could be the amine/boron adduct. The solid was treated with formic acid (90%, 10 g) and formaldehyde (37%, 50 g) at 90° C. overnight. The mixture was cooled by an ice-water bath and concentrated HCl (10 ml) was added. This mixture was distilled to remove about 35 ml of aqueous solution. The residue was treated with KOH (10%) to pH=11. The resulting mixture was extracted with methylene chloride (3×50 ml). The combined extracts were washed with water, dried over Na$_2$SO$_4$, and concentrated to give an oil. Distillation of the oil at reduced pressure gave di(4,4,5,5,6,6,7,7,7-nonafluoroheptyl)methylamine, 15 g, 98–105° C./200 Pa absolute, overall yield 50% (2 steps).

EXAMPLE 9

Synthesis of N-(4,4,5,5,6,6,7,7,7-nonafluoroheptl)-2,2,3,3-tetrahydroperfluoro-undecanamide A mixture of methyl 2,2,3,3-tetrahydroperfluoroundecanoate (16.2 g, 32 mmol) and 4,4,5,5,6,6,7,7,7-nonafluoroheptylamine (11.5 g, 41.5 mmol) was heated to slowly distill MeOH out through a 15 cm long column. Colorless liquid (1.25 g) was obtained by distillation at atmospheric pressure. After being cooled to room temperature, the residue in the reaction flask was solidified to a yellow solid which was dried at 100° C. for 6 h under vacuum to give N-(4,4,5,5,6,6,7,7,7-nonafluoroheptyl)-2,2,3,3-tetrahydroperfluoroundecanamide (23.0 g, 96% yield). $^{19}$F NMR (CDCl$_3$) –81.4 (t, J=10 Hz, 3F), –81.7 (t, J=10 Hz, 3F), –115.1 (m, 4F), –122.3 (m, 2F), –122.5 (m, 4F), –123.3 (m, 2F), –124.0 (m, 2F), –125.0 (m, 2F), –126.7 (m, 4F) ppm. $^1$H NMR (CDCl$_3$) 1.85 (m, 2H), 2.10 (m, 2H), 2.40–2.61 (m, 4H), 3.37 (q, J=7 Hz, 2H), 6.04 (br s, 1$^1$H) ppm. $^{13}$C NMR (CDCl$_3$) 21.0, 27.1 (t, J=22 Hz), 27.3, 28.5 (t, J=23 Hz), 38.9, 170.2, 108–123 (m) ppm. MS (m/e) 532 (M$^+$-C$_4$F$_9$, 48.7%), 475 (49.8%), 382 (M$^+$-C$_7$F$_{15}$, 46.5%), 332 (M$^+$-C$_8$F$_{17}$, 22.3%), 276 (30.9%), 219 (2.8%), 169 (18.8%), 119 (33.3%), 69 (100%).

EXAMPLE 10

Synthesis of N,N-Bis(4,4,5,5,6,6,7,7,7-nonafluoroheptyl)-4,4,5,5,6,6,7,7,7-nonafluoroheptanamide A mixture of methyl 4,4,5,5,6,6,7,7,7-nonafluoroheptanoate (12.2 g, 40 mmol) and bis(4,4,5,5,6,6,7,7,7-nonafluoroheptyl)amine (16.1 g, 30 mmol) was heated to slowly distill MeOH out through a 15 cm long column. Colorless liquid (4.5 g) was obtained by such distillation over a period 40 h. The reaction mixture was then pumped on full vacuum at 130° C. for 3 h to give N,N-bis(4,4,5,5,6,6,7,7,7-nonafluoroheptyl)-4,4,5,5,6,6,7,7,7-nonafluoroheptanamide (14.6 g, 60%). $^{19}$F NMR (CDCl$_3$) –81.6 (m, 9F), –114.6 (m, 2F), –114.9 (m, 2F), –115.1 (m, 2F), –125.0 (m, 6F), –126.6 (m, 6F) ppm. $^1$H NMR (CDCl$_3$) 1.90 (m, 4H), 2.12 (m, 4H), 2.44–2.64 (m, 4H), 3.42 (m, 4H) ppm. $^{13}$C NMR (CDCl$_3$) 18.9, 20.1, 24.1, 26.9 (t, J=23 Hz), 28.1 (t, J=22 Hz), 28.5 (t, J=22 Hz), 45.4, 47.0, 108–123 (m), 169.8 ppm. Anal. Calcd. for C$_{21}$H$_{16}$F$_{27}$NO: C, 31.09; H, 1.99; N, 1.73; F 63.22. Found: C, 30.71; H, 2.06; N, 1.42; F, 62.69.

EXAMPLE 11

Synthesis of Tris(4,4,5,5,6,6,7,7,7-nonafluoroheptyl) amine

A 250-ml 3-necked flask equipped with a stir bar, condenser, nitrogen inlet and an addition funnel was charged with LiAlH$_4$ (1.3 g) and 20 ml THF. To the mixture was added a THF (30 ml) solution of N,N-bis(4,4,5,5,6,6,7,7,7-nonafluoroheptyl)-4,4,5,5,6,6,7,7,7-nonafluoroheptanamide (20.6 g, 25.4 mmol) dropwise at RT. The resulting mixture was refluxed for 30 min. After being cooled, the mixture was carefully treated with water (3 ml) to decompose excess LiAlH$_4$. Another 50 ml water were added and the mixture was extracted with ether (3×100 ml). The combined ether extracts were washed with water, dried over Na$_2$SO$_4$, concentrated to give a residue which was distilled to afford tris(4,4,5,5,6,6,7,7,7-nonafluoroheptyl)amine, 17.5 g, yield 86%, bp 153–155° C./270 Pa absolute. $^{19}$F NMR (CDCl$_3$) –81.8 (tt, J=10, 3 Hz, 9F), –115.2 (m, 6F), –125.3 (m, 6F), –126.7 (m, 6F) ppm. $^1$H NMR (CDCl$_3$) 1.92 (m, 6H), 2.10 (m, 6H), 2.48 (t, J=6 Hz, 6H) ppm. $^{13}$C NMR (CDCl$_3$) 18.3, 28.7 (t, J=23 Hz), 52.9, 108–123 (m) ppm. Anal. Calcd. for C$_{21}$H$_{18}$F$_{27}$N: C, 31.63; H, 2.28; N, 1.76; F 64.33. Found: C, 31.49; H, 2.52; N, 1.77; F, 64.52. MS (m/e) 550 (M$^+$-C$_4$F$_9$(CH$_2$)$_2$, 100%), 512 (0.4%), 462 (0.6%), 362 (0.8%), 290 (11.3%), 276 (1.9%), 219 (0.3%), 169 (3.9%), 119 (7.1%), 69 (23.7%).

EXAMPLE 12

Synthesis of Tris(4,4,5,5,6,6,7,7,7-nonafluoroheptyl) methyl Ammonium Chloride

A mixture of tris(4,4,5,5,6,6,7,7,7-nonafluoroheptyl) amine (16.5 g, 20.7 mmol), methyl iodide (12 g, 85 mmol) and 30 ml of ethanol was refluxed for 24 h. The mixture was concentrated on a rotary evaporator to give the solid ammonium iodide. The iodide in methanol was converted to the chloride form by passing through a column packed with Amberlite® IRA 400 (Cl) ion exchange resin. The column effluent was collected and concentrated, then dried on vacuum overnight to afford 15.0 g of tris(4,4,5,5,6,6,7,7,7-nonafluoroheptyl) methyl ammonium chloride, yield 85%. $^{19}$F NMR (CD$_3$OD) –83.4 (t, J=10, Hz, 9F), –116.0 (m, 6F), –126.1 (m, 6F), –127.9 (m, 6F) ppm. $^1$H NMR (CD$_3$OD) 2.12 (m, 6H), 2.36 (m, 6H), 3.18 (s, 3H), 3.54 (m, 6H) ppm. $^{13}$C NMR (CD$_3$OD) 15.5, 28.8 (t, J=23 Hz), 53.7, 62.2, 108–123 (m) ppm. Anal. Calcd. for C$_{22}$H$_{21}$F$_{27}$NCl: C, 31.17; H, 2.50; N, 1.65; F, 60.50; Cl, 4.18. Found: C, 31.09; H, 2.45; N, 1.60; F, 60.53; Cl, 3.96.

EXAMPLE 13

Synthesis of (4,4,5,5,6,6,7,7,7-Nonafluoroheptyl)-(4,4,5,5,6,6,7,7,8,8,9,9,10,10,11,11,11-heptadecafluoroundecyl)amine)

A 250-ml 3-necked flask equipped with a stir bar, condenser, nitrogen inlet and an addition funnel was charged with LiAlH$_4$ (1.9 g) and 10 ml THF. To the mixture was added a THF (50 ml) solution of N-(4,4,5,5,6,6,7,7,7-nonafluoroheptyl)-4,4,5,5,6,6,7,7,8,8,9,9,10,10,11,11,11-heptafluoroundecanamide (22.8 g, 30.4 mmol) dropwise at RT. The resulting mixture was refluxed for 2 h. After being cooled, the mixture was carefully treated with water (3 ml) to decompose excess $LiAlH_4$. Another 50 ml of water were added and the mixture was extracted with ether (3×50 ml). The combined ether extracts were washed with water, dried over $Na_2SO_4$, concentrated to give a residue which was distilled to afford (4,4,5,5,6,6,7,7,7-nonafluoroheptyl)-(4,4,5,5,6,6,7,7,8,8,9,9,10,10,11,11,11-heptadecafluoroundecyl) amine, 13.1 g, yield 59%, bp 151–156° C./270 Pa absolute.

$(C_4F_9CH_2CH_2CH_2)(C_8F_{17}CH_2CH_2CH_2)NH$: $^{19}F$ NMR ($CDCl_3$) −81.5 (t, J=10 Hz, 3F), −81.8 (tt, J=10, 3 Hz, 3F), −114.9 (m, 2F), −115.1 (m, 2F), −122.2 (m, 2F), −122.4 (m, 4F), −123.7 (m, 2F), −124.1 (m, 2F), 125.1 (m, 2F), −126.7 (m, 4F) ppm. $^1H$ NMR ($CDCl_3$) 2.68 (t, J=6 Hz, 4H), 2.16 (m, 4H), 1.75 (m, 4H), 0.94 (br s, 1H) ppm. $^{13}C$ NMR ($CDCl_3$) 21.1, 28.9 (t, J=22 Hz), 29.0 (t, J=22 Hz), 48.5, 108–123 (m) ppm. MS (m/e) 518 ($M^+-C_4F_9$, 0.1%), 504 (0.60%), 490 (42%), 304 (0.1%), 290 (100%), 219 (0.4%), 169 (2.4%), 119 (4.4%), 69 (13.8%), Anal. Calcd. for $C_{18}H_{13}NF_{26}$: C, 29.32; H, 1.78; N, 1.90. Found: C,29.31; H,1.85; N,1.76.

EXAMPLE 14

Synthesis of (4,4,5,5,6,6,7,7,7-Nonafluoroheptyl)-(4,4,5,5,6,6,7,7,8,8,9,9,10,10,11,11,11-heptadecafluoroundecyl)methylamine A solution of(4,4,5,5,6,6,7,7,7-nonafluoroheptyl)-(4,4,5,5,6,6,7,7,8,8,9,9,10,10,11,11,11-heptadecafluoroundecyl) amine (11.0 g) and formic acid (90%, 4.5 g) was cooled in an ice-water bath and 24 ml of formaldehyde (37% weight) was added. The solution was slowly heated to 90° C. and maintained overnight. (Foaming and gas evolution at 60–75° C.). Concentrated hydrochloric acid (3 ml) was added and 7 ml of solution were removed by distillation. The remaining solution was cooled and treated with KOH (aq. 10%) to pH 11. The mixture was extracted with methylene chloride (3×100 ml). The combined methylen chloride extracts were washed with water (2×50 ml), dried over sodium sulfate, and concentrated under vacuum to give a residue. Distillation of the residue at reduced pressure gave 10.1 g of (4,4,5,5,6,6,7,7,7-nonafluoroheptyl)-(4,4,5,5,6,6,7,7,8,8,9,9,10,10,11,11,11-heptadecafluoroundecyl)methylamine, bp 138–141/ 270 Pa absolute, yield 90%. $^{19}F$ NMR ($CDCl_3$) −81.5 (t, J=10 Hz, 3F), −81.8 (tt, J=10, 3 Hz, 3F), −114.9 (m, 2F), −115.2 (m, 2F), −122.3 (m, 2F), −122.5 (m, 4F), −123.3 (m, 2F), −124.3 (m, 2F), −125.2 (m, 2F), −126.7 (m, 4F) ppm. $^1H$ NMR ($CDCl_3$) 2.40 (t, J=6 Hz, 4H), 2.18 (s, 3H), 2.13 (m, 4H), 1.75 (m, 4H) ppm. $^{13}C$ NMR ($CDCl_3$) 18.4, 28.6 (t, J=22 Hz), 28.8 (t, J=22 Hz), 41.3, 56.5, 108–123 (m) ppm. MS (m/e) 532 ($M^+-C_4F_9$, 0.2%), 518 ($M^+-CH_2C_4F_9$, 0.8%), 504 (89.1%), 304 (100%), 219 (0.7%), 169(4.5%), 119 (7.9%), 69 (24.4%). Anal. Calcd. for $C_{19}H_{15}NF_{26}$: C, 30.38; H, 2.01; N, 1.86. Found: C, 30.21; H, 2.08; N, 1.77.

EXAMPLE 15

Synthesis of (4,4,5,5,6,6,7,7,7-Nonafluoroheptyl)-(4,4,5,5,6,6,7,7,8,8,9,9,10,10,11,11,11-heptadecafluoroundecyl dimethylammonium chloride To a solution of (4,4,5,5,6,6,7,7,7-nonafluoroheptyl)-(4,4,5,5,6,6,7,7,8,8,9,9,10,10,11,11,11-heptadecafluoroundecyl)methylarnine (7.0 g, 9.4 mmol) and 15 ml of ethanol was added methyl iodide (3.0 g, 21 mmol) at room temperature. The mixture was stirred at 50° C. for 3 h. The solution was concentrated on a rotary evaporator to give solid ammonium iodide. The iodide in methanol (40 ml) was converted to the chloride form by passing through a column packed with Amberlite® IRA 400 (Cl) ion exchange resin. The column (effluent was collected and concentrated and dried under vacuum overnight to afford 6.7 g of (4,4,5,5,6,6,7,7,7-nonafluoroheptyl)-(4,4,5,5,6,6,7,7,8,8,9,9,10,10,11,11,11-heptadecafluoroundecyl) dimethylammonium chloride, yield 90%. $^{19}F$ NMR ($CD_3OD$) −80.7 (t, J=10 Hz, 3F), −81.0 (t, J=10 Hz, 3F), −113.4 (m, 2F), −113.7 (m, 2F), −121.0 (m, 2F), −121.2 (m, 4F), −122.1 (m, 2F), −122.7 (m, 2F), −123.8 (m, 2F), −125.6 (m, 4F) ppm. $^1H$ NMR ($CD_3OD$) 2.12 (m, 4H), 2.35 (m, 4H), 3.16 (s, 6H), 3.50 (m, 4H) ppm. $^{13}C$ NMR ($CD_3OD$) 15.8, 28.8 (t, J=23 Hz), 51.7, 64.5, 108–123 (m) ppm. Anal. Calcd. for $C_{20}H_{18}F_{26}NCl$: C, 29.96; H 2.26; N. 1.75; F, 61.61; Cl, 4.42. Found: C, 29.81; H, 2.33; N, 1.85; F, 61.66; Cl, 4.33.

EXAMPLE 16

Synthesis of Bis(4,4,5,5,6,6,7,7,7-nonafluoroheptyl) octylamine

A 250-ml flask was charged with triethylamine (4.2 g, 42 mmol), bis(4,4,5,5,6,6,7,7,7-nonafluoroheptyl)amine (18.4 g, 34.3 mmol), and 30 ml THF. To the mixture was added $C_7H_{15}COCl$ (6.0 g, 37 mmol) slowly at RT. The resulting mixture was stirred at RT for 1 h. Hexane (100 ml) and water (50 ml) were added to the flask. The mixture was then stirred at RT for 10 min. The bottom layer was isolated and extracted with hexane (50 ml). The extract from this was combined with the top layer and washed with HCl (1 N), water, KOH (aq. 5%) and water until pH=7, dried over $Na_2SO_4$, and concentrated to give a residue. The residue was pumped on full vacuum at 140° C. for 2 h to give a yellow oil, 17.6 g. A 250-ml 3-necked flask equipped with a stir bar, condenser, nitrogen inlet and an addition funnel was charged with $LiAlH_4$ (3.0 g) ard 10 ml THF. To the mixture was added a THF (50 ml) solution of the above ye low oil dropwise at 5° C. The resulting mixture was refluxed for 2 hours. After being cooled, the mixture was carefully treated with water (10 ml) to decompose excess $LiAlH_4$. Another 50 ml of water were added and the mixture was filtered. The slurry gel was washed with hexane (3×50 ml). The combined filtrate and hexane washings were separated into two layers. The top layer was washed with water, dried over $Na_2SO_4$, concentrated to give a residue which was distilled to afford di(4,4,5,5,6,6,7,7,7-nonafluoroheptyl)octylamine, 15.6 g, yield 70%, bp 159° C./270 Pa absolute. $^{19}F$ NMR ($CDCl_3$) −81.7 (tt, J=10, 3 Hz, 6F), −115.1 (m, 4F), −125.2 (m, 4F), −126.7 (m, 4F) ppm. $^1H$ NMR ($CDCl_3$) 0.88 (t, J=7 Hz, 3H), 1.27 (m, 10H), 1.39 (m, 2H), 1.71 (m, 4H), 2.38 (t, J=7 Hz, 2H), 2.46 (t,J=7 Hz, 4H) ppm. $^{13}C$ NMR ($CDCl_3$) 14.0, 18.4, 22.7, 27.2, 27.5, 28.7 (t, J=22 Hz), 29.3, 29.6, 31.9, 53.0, 53.9, 108–123 (m) ppm. MS (m/e) 550 ($M^+-C_7H_{15}$, 100%), 402 (83%), 304 (78%), 290 (25%), 169 (2.0%), 119 (4.8%), 71 (10%) 69 (29%), 57 (35%). Anal. Calcd. for $C_{22}H_{29}F_{18}N$: C, 40.67; H, 4.50; F, 52.66; N, 2.16. Found: C,40.58; H,4.54 F,53.02; N, 2.09.

EXAMPLE 17

Synthesis of Bis(4,4,5,5,6,6,7,7,7-nonafluoroheptyl) octyl methylammonium chloride To a solution of bis(4,4,5,5,6,6,7,7,7-nonafluoroheptyl) octylamine (13.5 g, 20.8 mmol) and 30 ml of ethanol was added methyl iodide (10.0 g, 70 mmol) at RT. The mixture was gently refluxed for 10 h. The solution was concentrated on a rotary evaporator to give solid ammonium iodide. The iodide in methanol (40 ml) was converted to the chloride form by passing through a column packed with Amberlite® IRA 400 (Cl) ion exchange resin. The column effluent was collected and concentrated and dried on vacuum overnight to afford 13.1 g of bis(4,4,5,5,6,6,7,7,7-nonafluoroheptyl) octylmethylammonium chloride, yield 89%. $^{19}$F NMR (CD$_3$OD) −80.9 (tt, J=10,3Hz, 6F), −113.7 (m, 4F), −123.7 (m, 4F), −125.5 (m, 4F) ppm. $^1$H NMR (CD$_3$OD) 0.89 t, J=7 Hz, 3H), 1.31 (m, 6H), 1.38 (m, 4H), 1.75 (m, 2H), 2.08 (m, 4H), 2.36 (m, 4H), 3.11 (s, 3H), 3.37 (m, 2H), 3.46 (m, 4H) ppm. $^{13}$C NMR (CD$_3$OD) 14.1, 15.2, 23.4, 23.7, 23.8, 27.5, 28.7 (t, J=24 Hz), 30.2, 32.9, 61.8, 63.6, 108–123 (m) ppm. Anal. Calcd. for C$_{23}$H$_{32}$F$_{18}$NCl: C, 39.47; H, 4.61; N, 2.00; F, 48.86; Cl, 5.07. Found: C, 38.95; H, 4.82; N, 2.11; F, 49.03; Cl, 4.73.

EXAMPLE 18

Synthesis of N,N-Dioctyl 4,4,5,5,6,6,7,7,8,8,9,9,10, 10,11,11,11-heptadecafluoroundecylamine A 250-ml flask was charged with triethylamine (5.9 g, 59 mmol), C$_8$F$_{17}$CH$_2$CH$_2$COCl (30.0 g, 58.8 mmol), and 30 ml THF. To the mixture was added dioctylamine (14.1 g, 58.5 mmol) slowly at RT. The resulting mixture was stirred at RT for 1 h. Hexane (100 ml) and water (50 ml) were added to the flask. The mixture was then stirred at RT for 10 min. The top layer was washed with HCl (1 N), water, KOH (aq. 5%) water until pH=8, dried over Na$_2$SO$_4$, and concentrated to give a residue. The residue was placed under full vacuum at 140° C. for 2 h to give the crude amide, 37.6 g.

A 250-ml 3-necked flask equipped with a stir bar, condenser, nitrogen inlet and an addition funnel was charged with LiAlH$_4$ (3.0 g) and 10 ml THF. To the mixture was added a THF (50 ml) solution of the crude amide dropwise at 5° C. The resulting mixture was refluxed for 2 h. After being cooled, the mixture was carefully treated with water (10 ml) to decompose excess LiAlH$_4$. Another 50 ml of water were added. The mixture was filtered. The slurry gel was washed with hexane (3×50 ml). The combined filtrate and hexane washings were separated into two layers. The top layer was washed with water, dried over Na$_2$SO$_4$, concentrated to give a residue which was distilled to afford dioctyl-4,4,5,5,6,6,7,7,8,8,9,9,10,10,11,11,11-heptadecafluoroundecylamine, 24.0 ) g, yield 59%, bp 157–163° C./40 Pa absolute. $^{19}$F NMR (CDCl$_3$) −81.3 (t, J=10 1 Hz, 3F), −114.6 (m, 2F), −122.4 (m, 6F), −123.5 (m, 2F), −124.0 (m, 2F), −126.7 (m, 2F) ppm. $^1$H NMR (CDCl$_3$) 0.88 (t, J=7 Hz, 6H), 1.27 (m, 20H), 1.40 (m, 2H), 1.71 (m, 2H), 2.12 (m, 2H), 2.37 (t, J=7 Hz, 4H), 2.45 (t, J=7 Hz, 2H) ppm. $^{13}$C NMR (CDCl$_3$) 14.0, 18.2, 22.7, 27.3, 27.6, 28.9 (t, J=22 Hz), 29.4, 29.6, 31.9, 53.1, 54.2, 108–123(m) ppm. MS (m/e) 602 (M$^+$−C$_7$H$_{15}$, 28%), 504 (15%), 254 (52%), 169 (3.4%), 119 (7.5%), 112 (39%), 71 (27%), 69 (60%), 57 (100%), 55 (65%).

EXAMPLE 19

Synthesis of Dioctyl 4,4,5,5,6,6,7,7,8,8,9,9,10,10, 11,11,11-Heptadecafluoroundecylmethylammonium chloride To a solution of dioctyl 4,4,5,5,6,6,7,7,8,8,9,9,10,10,11, 11,11-heptadadecafluoroundecylamine (18.5 g, 26.4 mmol) and 40 ml of ethanol was added methyl iodide (8.0 g, 56 mmol) at RT. The mixture was gently refluxed for 10 h. The solution was concentrated on a rotary evaporator to give solid ammonium iodide. The iodide in methanol (50 ml) was converted to the chloride form by passing through a column packed with Amberlite® IRA 400 (Cl) ion exchange resin. The column effluent was collected, concentrated and dried on vacuum overnight to afford 15.5 g of dioctyl 4,4,5,5,6, 6,7,7,8,8,9,9,10,10,11,11,11-heptadecatluoroundecylmethylammonium chloride, yield 78%. $^{19}$F NMR (CDCl$_3$) −81.4 (t, J=10 Hz, 3F), −114.1 (t, J=15 Hz, 2F), −122.2 (m, 2F), −122.5 (m, 4F), −123.3 (m 2F), −123.6 (m, 2F), −126.7 (m, 2F) ppm. $^1$H NMR (CDCl$_3$) 0.79 (t, J=7 Hz, 6H), 1.17 (m, 12H), 1.26 (m, 8H), 1.64 (m, 4H), 2.04 (m, 2H), 2.26 (m, 2H), 3.30 (s, 3H), 3.40 (m, 4H), 3.76 (m, 2H) ppm. $^{13}$C NMR (CDCl$_3$) 13.7, 14.5, 22.4, 26.2, 27.7 (t, J=22 Hz), 28.8, 28.9, 31.5, 48.7, 60.4, 61.7, 108–123 (m) ppm. Anal. Calcd. for C$_{28}$H$_{43}$F$_{17}$NCl: C, 44.72; H, 5.76; N, 1.86; F, 42.94; Cl, 4.71. Found: C, 44.51; H, 6.03; N, 1.88; F, 42.75; Cl, 4.53.

EXAMPLE 20

Disproportionation of 4,4,5,5,6,6,7,7,8,8,9,9,9-nonafluorononylamine: Synthesis of di(4,4,5,5,6,6, 7,7,8,8,9,9,9-nonafluorononyl)amine A 210-ml shaker tube was charged with 40 g of 4,4,5,5, 6,6,7,7,8,8,9,9,9-nonafluorononylamine, RuCl$_3$ (0.5 g), Ph$_3$P (1.2 g) and 40 ml THF. The mixture was heated at 240° C. for 24 h, then at 110° C. under 10.3 MPa pressure of hydrogen for 2 h. After being cooled to RT, the mixture was filtered to removed the catalyst. The filtrate was distilled to remove THF and distilled at reduced pressure to give di(4,4,5,5,6,6,7,7,8,8,9,9,9-nonafluorononyl)amine, 24 g, 61%, bp 119–124° C./130 Pa absolute. $^{19}$F NMR (CDCl$_3$) −81.4 (tt, J=10, 2 Hz, 6F), −114.9 (m, 4F), −122.4 (m, 4F), −123.4 (m, 4F), −124.1 (m, 4F), −126.7 (m, 4F) ppm. $^1$H NMR (CDCl$_3$) 2.69 (t, J=7 Hz, 4H), 2.17 (tt, J=19, 8 Hz, 4H), 1.76 (m, 4H), 0.85 (br s, 1H) ppm. $^{13}$C NMR (CDCl$_3$) 20.8 (t, J=3 Hz), 28.6 (t, J=22 Hz), 48.4 (s), 106.7–122.9 ppm. MS (m/e) 468 (M$^+$−C$_5$F$_{11}$, 1.6%), 404 (1.1%), 390 (100%), 169 (3.3%), 119 (9.2%), 100 (3.1%), 69 (40.8%), 57 (5.5%). Anal. Calcd. for C$_{18}$H$_{13}$F$_{26}$N: C, 29.32; H, 1.78; N, 1.90; F, 67.00. Found: C, 29.45; H, 1.96; N, 1.72; F, 66.95.

What is claimed is:

1. A compound of the formula (I), (II), or (III) wherein formula (I) is

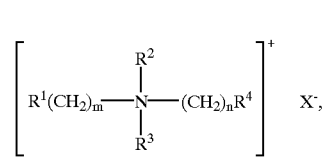

wherein formula (II) is

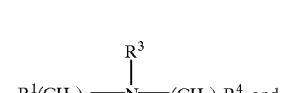

wherein formula (III) is

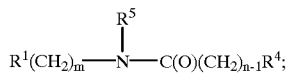
(III)

wherein:
m and n are each independently integers of 3 through 10;
R$^1$ and R$^4$ are each independently fluoroalkyl;
R$^2$ is alkyl;
R$^3$ is alkyl or R$^1$(CH$_2$)$_m$—;
R$^5$ is R$^1$(CH$_2$)$_m$—; and
X is an anion.

2. The compound as recited in claim 1 which is (I).

3. The compound as recited in claim 2 wherein R$^2$ is methyl, both R$^1$ and R$^4$ are perfluoro-n-alkyl containing 1 though 10 carbon atoms, R$^3$ is methyl or R$^1$(CH$_2$)$_m$—, and m and n are 3.

4. The compound as recited in claim 1 which is (II).

5. The compound as recited in claim 4 wherein R$^2$ is methyl, both R$^1$ and R$^4$ are perfluoro-n-alkyl containing 1 though 10 carbon atoms, and m and n are 3.

6. The compound as recited in claim 1 which is (III).

7. The compound as recited in claim 4 wherein R$^2$ is methyl, both R$^1$ and R$^4$ are perfluoro-n-alkyl containing 1 though 10 carbon atoms, and m and n are 3.

8. The compound as recited in claim 1 wherein R$^2$ is n-alkyl containing 1 through 10 carbon atoms, R$^1$ and R$^4$ are perfluoroalkyl, and m and n are 3.

9. The compound as recited in claim 8 wherein R$^2$ is methyl and R$^3$ is methyl or R$^1$(CH$_2$)$_m$—.

* * * * *